(12) United States Patent
Cronk et al.

(10) Patent No.: US 6,276,360 B1
(45) Date of Patent: *Aug. 21, 2001

(54) MEDICATED NASAL DILATOR

(76) Inventors: Peter J. Cronk; Kristen Cronk, both of 919 McElwee Rd., Moorestown, NJ (US) 08057

(*) Notice: Subject to any disclaimer, the term of this patent is extended or adjusted under 35 U.S.C. 154(b) by 0 days.

This patent is subject to a terminal disclaimer.

(21) Appl. No.: 09/388,591

(22) Filed: Sep. 2, 1999

Related U.S. Application Data

(63) Continuation of application No. 08/942,797, filed on Oct. 2, 1997, now abandoned, which is a continuation of application No. 08/791,760, filed on Jan. 29, 1997, now Pat. No. 5,706,800.

(51) Int. Cl.$^7$ .................................................. A61M 15/00
(52) U.S. Cl. .............................. 128/200.24; 128/204.13; 128/207.14; 606/199; 606/204.45
(58) Field of Search .................... 128/846, 848, 128/200.24, 207.18; 606/204.45; 602/902

(56) References Cited

U.S. PATENT DOCUMENTS

| | | | |
|---|---|---|---|
| Re. 35,408 | 12/1996 | Petruson | 128/858 |
| D. 310,565 | 9/1990 | Petruson | |
| 3,567,118 | 3/1971 | Shepherd et al. | 239/6 |
| 3,655,129 | 4/1972 | Seiner | 239/60 |
| 3,688,985 | 9/1972 | Engel | 239/54 |
| 3,710,799 | 1/1973 | Caballero | 128/342 |
| 3,846,404 | 11/1974 | Nichols | 260/230 |
| 3,909,444 | 9/1975 | Anderson et al. | 428/402 |
| 3,954,963 | 5/1976 | Kuderna, Jr. | 424/76 |
| 3,965,033 | 6/1976 | Matsukawa et al. | 252/316 |
| 3,985,298 | 10/1976 | Nichols | 239/54 |
| 3,994,439 | 11/1976 | Van Breen et al. | 239/54 |
| 4,016,254 | 4/1977 | Seager | 424/33 |
| 4,067,824 | 1/1978 | Tent et al. | 252/522 |
| 4,128,507 | 12/1978 | Mitzner | 252/522 |
| 4,136,250 | 1/1979 | Mueller et al. | 528/29 |
| 4,267,831 | 5/1981 | Aguilar | 128/203 |
| 4,339,356 | 7/1982 | Whyte | 252/522 |
| 4,356,115 | 10/1982 | Shibanai et al. | 252/522 A |
| 4,414,977 | 11/1983 | Rezakhany et al. | 606/199 |
| 4,492,644 | 1/1985 | Matsumoto et al. | 252/522 |
| 4,523,589 | 6/1985 | Krauser | 128/203 |
| 4,597,959 | 7/1986 | Barr | 424/19 |

(List continued on next page.)

FOREIGN PATENT DOCUMENTS

| | | |
|---|---|---|
| 7048250A | 2/1995 | (JP) . |
| 7215847A | 8/1995 | (JP) . |
| 10120555A | 5/1998 | (JP) . |
| WO98/06360 | 2/1998 | (WO) . |
| WO98/27897 | 7/1998 | (WO) . |

OTHER PUBLICATIONS

Letter from Daniel E. Cohen, President & CEO of CNS, Inc. dated Jun. 1, 1998.

(List continued on next page.)

*Primary Examiner*—Michael A. Brown
(74) *Attorney, Agent, or Firm*—Duane Morris & Heckscher LLP

(57) ABSTRACT

Nasal dilators and methods for improving the breathing of individuals are provid. The dilator includes an elongated substrate having top and bottom surfaces and a pressure-sensitive adhesive disposed on the bottom surface. The elongated substrate can be made with resilient or spring material, or a resilient member can be bonded to the substrate to provide a gentle expanding force to the nasal wall tissue when the dilator is adhesively attached to the nose. This invention further includes an aromatic or transdermal substance, or both, disposed on the dilator to further improve breathing. Ideal aromatic substances include camphor and menthol. The aromatic substance can be disposed in a segregate form or in body activatable composition.

22 Claims, 2 Drawing Sheets

U.S. PATENT DOCUMENTS

| | | | |
|---|---|---|---|
| 4,638,043 | 1/1987 | Szycher et al. | 528/75 |
| 4,808,466 | 2/1989 | Kotani et al. | 428/254 |
| 4,842,761 | 6/1989 | Rutherford | 252/90 |
| 4,880,690 | 11/1989 | Szycher et al. | 428/224 |
| 4,927,631 | 5/1990 | Bates | 424/195 |
| 4,971,798 | 11/1990 | Coia et al. | 424/440 |
| 5,043,161 | 8/1991 | Scarpelli et al. | 424/401 |
| 5,071,704 | 12/1991 | Fischel-Ghodsian | 428/354 |
| 5,081,104 | 1/1992 | Orson, Sr. | 512/3 |
| 5,175,152 | 12/1992 | Singh | 514/162 |
| 5,223,251 | 6/1993 | Nichols | 424/69 |
| 5,234,610 | 8/1993 | Gardlik et al. | 252/8.6 |
| 5,322,689 | 6/1994 | Hughes et al. | 424/401 |
| 5,336,665 | 8/1994 | Garner-Gray et al. | 512/4 |
| 5,378,468 | 1/1995 | Suffis et al. | 424/401 |
| 5,380,707 | 1/1995 | Barr et al. | 512/17 |
| 5,391,374 | 2/1995 | Charbonneau et al. | 424/401 |
| 5,455,043 | 10/1995 | Fischel-Ghodsian | 424/448 |
| 5,476,019 | 12/1995 | Johnson | 128/200 |
| 5,479,944 | 1/1996 | Petruson | 128/858 |
| 5,500,154 | 3/1996 | Bacon et al. | 252/551 |
| 5,508,259 | 4/1996 | Holzner et al. | 512/4 |
| 5,533,503 * | 7/1996 | Doubek | 128/200.24 |
| 5,536,263 | 7/1996 | Rolf et al. | 604/307 |
| 5,546,929 * | 8/1996 | Muchin | 128/200.24 |
| 5,549,103 * | 8/1996 | Johnson | 128/200.24 |
| 5,569,679 | 10/1996 | Jacob | 514/711 |
| 5,585,343 | 12/1996 | McGee et al. | 512/1 |
| 5,611,333 * | 3/1997 | Johnson | 128/200.24 |
| 5,622,992 | 4/1997 | Beck | 514/613 |
| 5,626,852 | 5/1997 | Suffis et al. | 424/401 |
| 5,669,377 | 9/1997 | Fenn | 128/200 |
| 5,706,800 | 1/1998 | Cronk et al. | 128/200 |
| 5,711,941 | 1/1998 | Behan et al. | 424/65 |
| 5,720,966 | 2/1998 | Ostendorf | 424/402 |
| 5,723,420 | 3/1998 | Wei et al. | 510/101 |
| 5,725,865 | 3/1998 | Mane et al. | 424/401 |
| 5,740,798 | 4/1998 | McKinney | 128/206 |
| 5,741,510 | 4/1998 | Rolf et al. | 424/448 |
| 5,868,131 | 2/1999 | Murchie | 128/204.13 |
| 5,890,486 | 4/1999 | Mitra et al. | 128/200.24 |

OTHER PUBLICATIONS

Letter from Daniel E. Cohen, M.D. (Chairman & CEO of CNS, Inc.) to Roland S. Spangler, Ph.d (Emerging Growth Equities, LLC) dated Sep. 9, 1996.

3M–CNS, Inc., distributtion Agreement dated Aug. 2, 1995.

3M–CNS, Inc., Supply Agreement dated Dec. 31, 1995.

Letter from Ronald Spangler, Ph.D (Managing Director of Emerging Growth Equities, LLC) to Richard E. Jahnke (CNS, Inc.) dated Aug. 27, 1996.

Memo from John Neveaux (JLN Associates) to Andy Anderson dated Oct. 30, 1992.

CNS, Inc. prospectus dated Mar. 29, 1996 (highlighted page 25).

Buchbauer G., Jirovetz L., Jaeger W., Plank C., Dietrich H., Title "Fragrance Compounds and Essential Oils with Sedative Effects Upon Inhalation", Source: Journal of Pharmaceutical Sciences 82 (6), 1993, pp. 660–664. (Abstract only).

Nagahara A., Benjamin H., Storkson, J., Krewson J., Sheng K., Liu W., Pariza M., Title "Inhibition of Benzo–A–Pyrene–Induced Mouse Forestomach Neoplasia by a Principal Flavor Component of Japanese–Style Fermented Soy Sauce", Source: Cancer Research 52 (7), 1992, pp. 1754–1756. (Abstract only).

Halim A.F ., Mashaly M.M., Sandra P., Title "Constituents of the Essential Oil of Mentha–Microphylla C. Koch.", Source: Egyptian Journal of Pharmaceutical Sciences 31 (1–4), 1990, pp. 437–442. (Abstract only).

Jungnickel P.W., Shaefer M.S., Maloney P.A., Campbell J.R., Shawaryn G.G., Goris G.B., Oliphant T.H., Title "Blind Comparison of Patient Preference for Flavored Colestid Granules and Questran Light", Source: Annals of Pharmacotherapy 27 (6), 1993, pp. 700–703. (Abstract only).

Schaller M., Korting H.C., Title "Allergic Airborne Contact Dermatitis from Essential Oils Used in Aromatherapy", Source: Clinical & Experimental Dermatology 20 (2), 1995, pp. 143–145. (Abstract only).

Mukhtar H., Katiyar S.K., Agarwal R., Title "Green Tea and Skin–Anticarcinogenic Effects", Source: Journal of Investigative Dermatology 102 (1), 1994, pp. 3–7. (Abstract only).

Everett T., Dennis M., Ricketts E., Title "Physiotherapy in Mental Health: A Practical Approach", Source: Everett T., M. Dennis and E. Ricketts (Ed.) Physiotherapy in Mental Health: A Practical Approach. xv+424p. Butterwoth–Heinemann Ltd., London, England, UK; Butterworth–Heinemann: Newton, Massachusetts, USA. XV+424P. ISBN 0–7506–1700–4. 1995. (Abstract only).

Komori T., Fujiwara R., Tanida M., Nomura J., Yokoyama M.M., Title "Effects of Citrus Fragrance on Immune Function and Depressive States", Source: Neuroimmunomodulation 2(3), 1995, pp. 174–180. (Abstract only).

Lis Balchin, Hart S., Title: A Preliminary Study of the Effect of Essential Oils on Skeletal and Smooth Muscle in Vitro, Source: Journal of Ethnopharmacology 58(3), 1997, pp. 183–187. (Abstract only).

Lindsay W.R., Pitcaithly D., N. Buntin., L. Broxholme, S. Ashby M., Title "A Comparison of the Effects of Four Therapy Procedures on Concentration and Responsiveness in People with Profound Learning Disabilities", Source: Journal of Intellectual Disability Research 41 (3), 1997, pp. 201–207. (Abstract only).

Morice A.H., Marshall A.E., Higgins K.S., Grattna T.J., Title "Effect of Inhaled Menthol on Citric Acid Induced Cough in Normal Subjects", Source: Thorax 49 (10), 1994, pp. 1024–1026. (Abstract only).

Eccles R., Griffiths D.H., Newton C.G., Tolley N.S., Title "The Effects of Menthol Isomers on Nasal Sensation of Airflow", Source: Clinical Otolaryngology & Allied Sciences (Oxford) 13 (1), 1988, pp. 25–30. (Abstract only).

Zaenker K.S., Toelle W., Bluemel G., Probst J., Title "Evaluation of Surfactant–Like Effects of Commonly Used Remedies for Colds", Source: Respiration 39 (3), 1980, pp. 150–157. (Abstract only).

Cohen B.M., Dressler W.E., Title: "Acute Aromatics Inhalation Modifies the Airways Effects of the Common Cold", Source: Respiration 43 (4), 1982, pp. 285–293. (Abstract only).

Eccles R., Jones A.S., Title "The Effect of Menthol on Nasal Resistance to Air Flow", Source: Journal of Laryngology & Otology 97 (8), 1983, pp. 705–709. (Abstract only).

Burrow A., Eccles R., Jones A.S., Title "The Effects of Camphor Eucalyptus and Menthol Vapor on Nasal Resistance to Air Flow and Nasal Sensation", Source: Acta Oto–Laryngologica 96 (1–2), 1983, pp. 157–162. (Abstract only).

Gal Fuzy M., Szente L., Szejtli J., Harangi J., Title "Cyclodextrin–Stabilized Volatile Substances for Inhalation Therapy", Source: Pharmazie 39 (8), 1984, pp. 558–559 (Abstract only).

Khadzhai Ya I., Bashura G.S., Sheherbakova N.R., Aslanyants A.A., Kuznetsova V.F., Title "The New Aerosol Preparation Camphomene", Source: Khimiko–Farmatsevticheskii Zhurnal 11 (1), 1977, pp. 147–149, (Abstract only).

Robinson M.K., Cruze C.A., Title "Preclinical Skin Sensitization Testing of Antihistamines: Guinea Pig and Local Lymph Node Assay Responses", Source: Food & Chemical Toxicology 34 (5), 1996, pp. 495–506. (Abstract only).

Radler S., Blaschek G., Title "Transdermal Absorption of Dimethindene in Man", Source: Achiv der Pharmazie (Weinheim) 328 (2), 1995, pp. 127–129. (Abstract only).

Binger Str., Title "Accumulation of Granulocytes in the Lung and Skin of Guinea Pigs: Inhibition by the Anti–H–1 Antiallergic Agent Epinastine", Source: Arzneimittel–Forschung 44 (12), 1994, pp. 1338–1342. (Abstract only).

Harada S., Takahashi Y., Nakagawa H., Title "Transdermal Administration of Emedastine", Source: Biological & Pharmaceutical Bulletin 16 (9), 1993, pp. 884–888. (Abstract only).

Robinson M.K., Parsell K.W., Breneman D.L., Cruze C.A., Title "Evaluation of the Primary Skin Irritation and Allergic Contact Sensitization Protential of Transdermal Triprolidine", Source: Fundamental & Applied Toxicology 17 (1), 1991, pp. 103–119. (Abstract only).

Miles M.V., Balasubramanian R., Pittman A.W., Grossman S.H., Pappa K.A., Smith M.F., Wargin W.A., Findlay J.W.A., Poust R.J., Frosolono M.F., Title "Pharmacokinetics of Oral and Transdermal Triprolidine", Source: Journal of Clinical Pharmacology 30 (6), 1990, pp. 572–575. (Abstract only).

B. Petruson, Title: "Two New Ways for Nasal Administration of Drugs with the Nasal Dilator Nozovent", Source: ENT–Department, University of Gőtteborg, Sahlgren's Hospital, 413 45 Gőteborg, Sweden.

"Breathe Right" Nasal Strips, Manufactured by CNS, Inc., Chanhassen, MN.

Article entitled "New Device Offers Relief for Snorers".

Letters from Ronald S. Spangler, Ph.D to Richard E. Jahnke (former president of CNS, Inc.) dated Aug. 27, 1996.

Letter from Daniel E. Cohen, Chairman & CEO of CNS, Inc. to Ronald Spangler, Ph.D dated Sep. 9, 1996.

CNS, Inc.–3M Supply Agreement, SEC filing date: Dec. 31,1995.

CNS, Inc.–3M Distribution Agreement, SEC filing date Dec. 31, 1995 (highlighted pp. 49 and 50).

Ognyanov I., Fam Thi Bin Min, Todorova M., Kuleva L., Title "Chemotypes in Some Bulgarian Populations of Chrysanthemum–Vulgare L. Bernh.", Source: Comptes Rendus de L'Academie Bulgare des Sciences 45 (4), 1992, pp. 29–31.

Zheng G.Q., Kenney P.M., Zhang J., Lam L.K.T., Title "Inhibition of Benzo–A–Pyrene–Induced Tumorigenesis by Myristicin A Volatile Aroma Constituent of Parsley Leaf Oil", Source: Carcinogenesis (Eynsham) 13 (10), 1992, pp. 1921–1923. (Abstract only).

Teopista N., Title "The Use of Aroma Therapy A.T. in the Management of People with Aids PWAS", Source: IXth International Conference on Aids and the IVth Std. World Congres. IXth International Conference on Aids in Affiliation with the IVth Std. World Congress Meeting, Berlin, Germany, Jun. 6–11, 1993. 649P. IXth International Conference on Aids: Berlin, Germany, 1993, 497. (Abstract only).

CNS, Inc.–3M Distribution Agreement, SEC filing date Dec. 31, 1995 (highlighted pp. 49 and 50).

CNS Inc., *Breathe Righ®Instructions*, 1995.

"Breathe Right", Nasal Strips, Manufactured by CNS, Inc., Chanhassen, MN.

B4–U–BUY™ FYI,http://www.b4–u–buy.com/snorers.html, *New Device Offers Relief For Snorers*.

Sigma Online Catalog, *Nozovent*.

Hornung et al., "Effect of Nasal Dilators on Perceived Odor Intensity", *Chem Senses* 22:177–180, Apr. 1997.

Hornung et al., "Effect of Nasal Dilators on Olfaction: I Nasal Structure and Sniffing Stragegies", pp 1–8, unpublished.

Hornung et al., "Effect of Nasal Dilators on Olfaction: II Threshold, Intensity and Identification", pp 1–7, unpublished.

\* cited by examiner

MEDICATED NASAL DILATOR

RELATED APPLICATION DATA

This application is a continuation of U.S. application Ser. No. 08/942,797, filed on Oct. 2, 1997, now abandoned, which in turn is a continuation of U.S. application Ser. No. 08/791,760, filed on Jan. 29, 1997, now U.S. Pat. No. 5,706,800, issued Jan. 13, 1998.

FIELD OF THE INVENTION

This invention relates to dilators for easing the breathing of patients, and more particularly to medicated nasal dilators for preventing outer wall tissue of nasal passages from drawing in during breathing while providing medication to the patient.

BACKGROUND OF THE INVENTION

Nasal dilators have been suggested for aiding breathing through the nose. There have been traditionally two types of dilators which have been effective in humans. One type uses small rings or cages connected to a resilient structure. The rings are inserted into each nasal passage while the resilient structure spreads to provide unobstructed breathing. These dilators have been criticized because they are often uncomfortable to wear. Since the cages or rings are inserted into contact with sensitive nasal tissue, they have been known to cause irritation and itching. Such devices are disclosed in U.S. Pat. No. 3,710,799 to Caballero and the NOZOVENT dilator disclosed in Petruson D310,565.

More recently, advancements have been made in nasal dilators which attach to the outer wall tissue of the nose and aide in preventing the inner nasal tissue from drawing in during breathing. Such dilators include a flexible strip of material adhesively attached to a substrate. The dilator is fastened to the nose and the resilient material acts to keep the left and right nasal passages from drawing in or collapsing during inhalation. This usually occurs due to a malformation, such as a deviated septum or due to swelling during allergic reactions and the like. Examples of nasal dilators which are adhesively attached to the outer skin of a human nose are disclosed in Doubek et al., U.S. Pat. No. 5,533,503 and Muchin, U.S. Pat. No. 5,546,929.

While conventional nasal dilators are being used by a greater number of people, there is still a need to further improve the breathing of those individuals to a greater degree than can be established by mere mechanical manipulation of their nasal tissue.

SUMMARY OF THE INVENTION

Nasal dilators and methods of easing breathing are provided by this invention. The first group of preferred dilators include an elongated substrate having a pair longitudinal sides, a pair of transverse ends and top and bottom surfaces. Disposed on the bottom surface of the substrate is a pressure sensitive adhesive. The substrate also includes a resilient member bonded to its surface to provide a gentle expanding force to a nasal wall tissue when the dilator is adhesively attached to a nose. In an important improvement over the prior art, an aromatic medication is disposed on a portion of the dilator so that it can be inhaled through the nose of the wearer during breathing.

This invention combines the spring action of adhesively applied nasal dilators with inhaleable aromatics. Such an accommodation has the potential to produce synergistic benefits for patients who have not been entirely satisfied by either non-medicated dilators, or over-the counter decongestant medication, some of which can cause drowsiness.

In another embodiment of this invention, a method of substantially preventing the wall tissue of a nose from drawing in during breathing is provided. The method includes providing a nasal dilator including a substrate having disposed thereon a pressure sensitive adhesive layer on a first surface and a resilient member bonded to a second surface. Impregnated into the substrate is an aromatic medication for helping the patient breathe easier. The method further includes applying the pressure sensitive adhesive layer across a nose whereby the resilient member provides a gentle expanding force to the nasal wall tissue while the aromatic medication is being inhaled.

Further embodiments of this invention include transdermal medications and resilient scrims or sheet layers bonded to the substrate for minimizing the expense of continuous processing of the dilators of this invention.

BRIEF DESCRIPTION OF THE DRAWINGS

The accompanying drawings illustrate preferred embodiments of the invention as well as other information pertinent to the disclosure, in which.

DETAILED DESCRIPTION OF THE INVENTION

This invention provides nasal dilators and methods for substantially preventing a nasal wall tissue of a nose from drawing in during breathing. As used herein, the term "aromatic" medication refers to substances and compounds which can be consumed by inhaling through the nose, such as a medicated vapor or gas. Such substances should have some efficacy in helping patients breathe easier or better.

Figure 1:
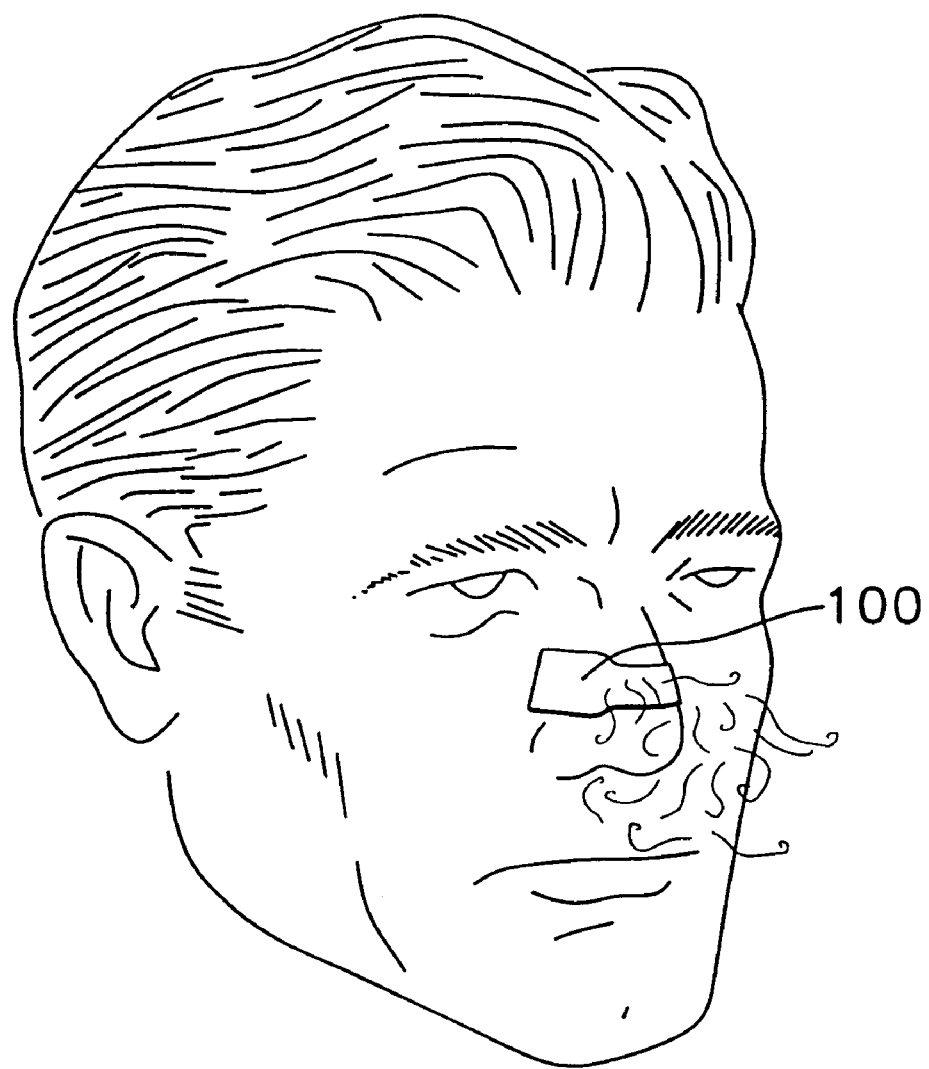
FIG. 1: is a partial front perspective view of a man wearing the preferred nasal dilator of this invention.
Figure 2:
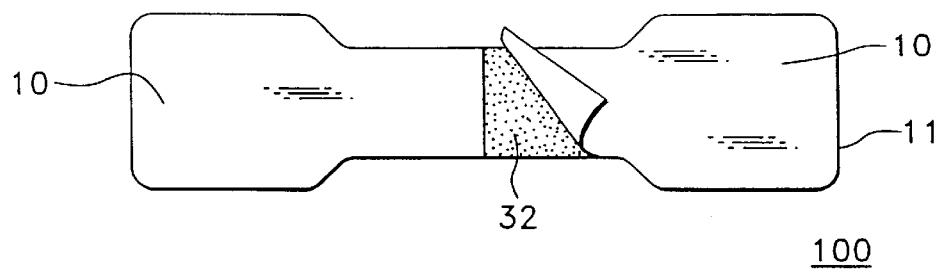
FIG. 2: is a top planar view the nasal dilator of this invention with a partial peel back view of the adhesive layer.
Figure 3:
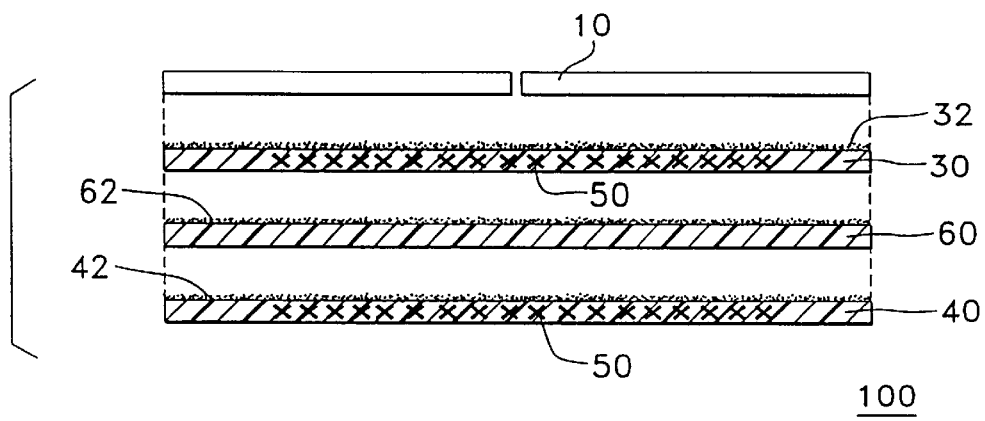
FIG. 3: is a side elevation, cross-sectional, exploded view of the nasal dilator of FIG. 2.
Figure 4:
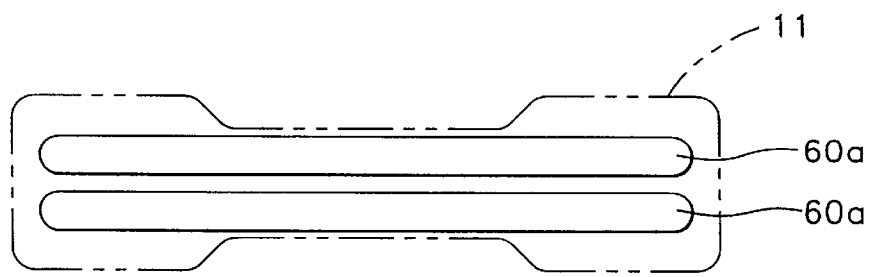
FIG. 4: is a top planar view of a preferred resilient member, including the periphery of the substrate of the nasal dilator in phantom.

With reference to the figures and in particular, FIGS. 1–3 thereof, there shown a preferred nasal dilator 100 sized to fit across the nose of the wearer so as to engage the outer wall tissue of the left and right nasal passages of the wearer. As shown in FIGS. 2–3 the nasal dilator 100 includes an elongated substrate 30 having a pair of longitudinal sides, a pair of transverse ends and top and bottom surfaces thereon. Disposed on a bottom surface of the substrate 30 is an adhesive layer 32 for permitting easy attachment to the wearer's skin. Also attached to the substrate is a resilient member 60 which provides a gentle expanding force to the nasal wall tissue when the dilator is adhesively attached to the nose. Finally, an aromatic medication 50 is disposed on a portion of the dilator so as to be inhaled through the nose of the wearer during breathing.

In further embodiments of this invention, the dilator 100 can include a backing layer 40. The backing layer 40 and resilient member 60 are desirably bonded to the substrate 30 using pressure sensitive adhesive layers 42 and 62. As shown in FIG. 3 the aromatic medication can be disposed on any surface of the dilator 100. Preferably the aromatic medication 50 is disposed on an absorbent layer portion of the dilator 100. The absorbent layer portion can be a separate absorbent layer or a portion of the elongated substrate 30 or backing layer 40. Alternatively, the aromatic medication can be disposed in one of the adhesive layers in an admixture or segregated form, and can be activated by contact with a human body, such as, for example, by being warmed by body heat. Finally, a release paper strip 10 can be added over the pressure sensitive adhesive layer 32 prior to packaging the strip for sale.

The elongated substrate 30 of this invention may include any thin, flexible, breathable material for maximizing comfort. Preferably this material permits the passage of air and moisture vapor, such as perspiration. The elongated substrate can include, for example, a woven or non-woven fabric material, such as non-woven, polyester fabric. One good example is a fabric produced by DuPont E. I. de Nemours & Co., Inc. under the trademark Sontara®. Alternatively, the elongated substrate 30 can include a thermoplastic woven or non-woven fabric, such as spunbonded polyethylene or polypropylene. The substrate 30 can also be treated with the aromatic medication 50 of this invention, along with a hydrophilic or hydrophobic additive for absorbing or repelling sweat or moisture on a selective basis.

Attached to the substrate 30 on the nose skin-facing side or bottom surface of the substrate 30 is an adhesive layer 32. This adhesive layer, along with optional adhesive layers 62 and 42 can be made of a pressure sensitive biocompatible adhesive material. As used herein, "pressure-sensitive" refers to any releasable adhesive or releasable tenacious means. Adhesive compositions suitable for nasal dilators include water-based pressure-sensitive adhesives, such as acrylate adhesives, thermoplastics "hot melt" adhesives, two-sided adhesive tape, elastomer-based adhesives, and acrylic adhesives. Good examples include 3M1509 double-sided medical tape provided by 3M Inc., St. Paul, Minn. This product is a double-sided transparent polyethylene film, coated on both sides with a hypoallergenic, pressure-sensitive acrylate adhesive, supplied on a paper liner. Of course, adhesive layers 62 and 42 need not be a pressure-sensitive type at all, since once the resilient member 60 and backing layer 40 are adhered to the substrate 30, it is undesirable for these layers to separate during application or removal of the dilator from the nose.

The resilient member 60 of this invention preferably includes one or more spring strips 60*a* which can be die-cut from spring ribbon material. Good examples of spring ribbon material include biaxially oriented polyester that is approximately 0.01 inches thick, but polyethylene or polypropylene strips of like thickness would also provide expanding force to the dilator 100. Fiber additions to the resin of the spring strips 60*a*, such as, glass, graphite, carbon or boron will also improve resiliency.

Figure 5:
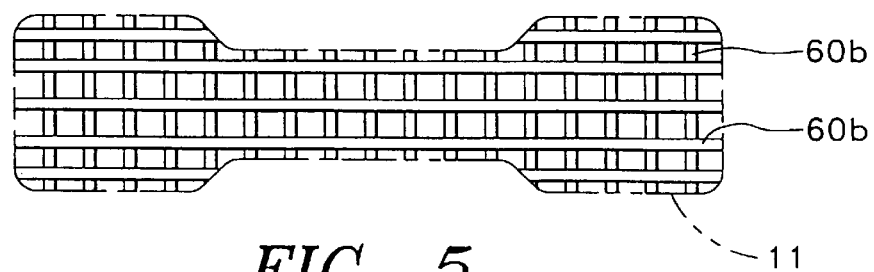
FIG. 5: is a top planar view of an alternative resilient member consisting of a reinforcing scrim also depicting the periphery of the substrate in phantom.

Alternatively, as shown in FIG. 5, a resilient layer, such as scrim 60*b* can be disposed within, or substantially along the perimeter 11 of the substrate 30 or outer peripheral region of the dilator 100. The resilient layer can be a woven oriented mat, fabric or material, or a non-woven mat material of fibers which are either adhesively or melt bonded together. Such fibers can include thermoplastic or thermosetting polymers. Examples include thermoplastic fibers, such as nylon, polyethylene, and polyester fibers, for example SPECTRA or COMPET fibers sold by Allied Signal Corp., Kevlar® 29, 49 or 149 aramid fibers sold by DuPont, glass, such as E-glass and S-Glass fibers, graphite fibers, carbon fibers, boron fibers, or combinations of these fibers. The resilient member, whether including spring strips 60*a* or a resilient scrim 60*b* or sheet layer (not shown) is preferably joined together in a webbing operation either by melt bonding, adhesive bonding or ultrasonic bonding. In conventional operations, a ribbon of resilient material and substrate material are adhesively joined together as they are fed into an overlapping position in a die or roller. Adhesive layers 42 and 62 are used to join the backing layer, resilient member 60 and elongated substrate 30 together prior to die-cutting to form the final periphery 11 of the dilator 100. The adhesive layers 42, 62 and 32 can be applied by spray, roll or knife, as is customary in the web-processing industry.

An important advantage of the resilient layer, such as scrim 60*b* or a sheet layer, as opposed to a pair of discrete spring strips 60*a* of this invention, is the elimination of a careful placement operation prior to die-cutting. Such an expensive step becomes unnecessary, since the resilient layer preferably conforms generally to the perimeter 11 of the final die-cut dilator. This can eliminate waste and minimize much of the expense of the webbing operation. It also provides for a more uniform spring action along most or all of the surface area of the dilator 100.

Additionally, this invention contemplates employing thermoplastic materials in the backing layer 40 and substrate 30, and alternatively, with respect to the resilient member 60 or layer. When thermoplastic materials are used, this invention enables inexpensive melt-bonding of the layers of material, with heat and pressure, to provide a composite nasal dilator structure. Melt-bonding could eliminate the need of additional adhesive layers 42 and 62 and provide a greater structural integrity to the dilator no matter what form of resilient member is employed. However, resilient scrim 60*b* is ideally suited for thermoplastic bonding of layers since it has pores for permitting softened thermoplastic material to bond between the fibers or filaments, further increasing the strength of the dilator 100, without requiring a lot of material.

In a further important aspect of this invention, the dilator can include an aromatic medication 50, transdermal medication, or both. Good examples of aromatic medications include camphor, eucalyptus oil, peppermint oil, menthol, methy salicylate, bornyl acetate, lavender oil, or a combination of these. Transdermal decongestants and antihistamines are also available, such as diphenhydramine and triprolidine transdermal antihistamine, available from Proctor and Gamble Co., Inc., Cincinnati, Ohio; others include ephedrine, dimethindene, epinastine, emedastine, and clonidine. These aromatic and transdermal medications can be mixed within adhesive layer 32, as in, for example, a dispersion-type transdermal patch formulation from acrylate copolymer adhesive or a lecithin gel based matrix. Alternatively, a rate controlling membrane could be used, such as Eudragit RL-100.

From the foregoing, it can be realized that this invention provides improved nasal dilators which include possibly synergistic combinations of mechanical and medicated aromatic or transdermal compositions. Also included are material processing improvements which add improved functionality and reduce the overall cost of the product. The dilators and methods of this invention are useful for helping individuals with deviated septums and athletes who desire more oxygen during a performance. Although various embodiments have been illustrated, this is for the purpose of describing, but not limiting the invention. Various modifications which will become apparent to one skilled in the art, are within the scope of this invention described in the attached claims.

What is claimed is:

1. A nasal dilator for substantially preventing a nasal wall tissue of a nose of a wearer from drawing in during breathing, comprising:

an elongated flexible substrate;

a resilient member bonded to said substrate to provide a gentle expanding force to said nasal wall tissue when said dilator is adhesively attached to said nose;

a pressure sensitive adhesive layer disposed on a bottom surface of said dilator; and a body activatable composition comprising an aromatic substance disposed on a portion of said dilator.

2. The nasal dilator of claim 1 wherein said aromatic substance comprises a medication.

3. The nasal dilator of claim 1 wherein said elongated flexible substrate comprises a breathable material.

4. The nasal dilator of claim 1 wherein said body activatable composition is adhesively applied to said flexible substrate.

5. The nasal dilator of claim 1 further comprising a hydrophilic additive disposed with said aromatic substance for absorbing sweat or moisture.

6. The nasal dilator of claim 1 wherein further comprising a hydrophobic additive disposed with said aromatic substance for repelling sweat or moisture.

7. The nasal dilator of claim 1 wherein said aromatic substance is disposed in an amount sufficient to create a synergistic effect on the breathing of said patient through the combination of mechanical and medicated dilation.

8. A method of manufacturing a nasal dilator, comprising:

providing a web of flexible, substrate material;

joining a resilient material to said substrate material in overlapping fashion, whereby said resilient material and substrate material are joined by heat, pressure, adhesive, or a combination thereof, to form a composite;

affixing an adhesive layer to a bottom surface of said composite;

applying an aromatic substance in a substantially body activatable composition to a surface of said composite; and cutting said composite to form a final periphery of said nasal dilator.

9. The method of claim 8 wherein said cutting step comprises die cutting said composite.

10. The method of claim 8 wherein said applying an aromatic substance step comprises spraying said aromatic substance onto said exterior surface of said composite.

11. A nasal dilator for substantially preventing a nasal wall tissue of a nose of a wearer from drawing in during breathing, comprising:

a thin, flexible, resilient member;

a medicated substance disposed in a substantially segregated form and affixed by an adhesive on an exterior surface of said member, said medicated substance comprising camphor, eucalyptus oil, peppermint oil, menthol, methylsalicylate, bornyl acetate, lavender oil, a transdermal antihistamine, a transdermal decongestant, or a combination thereof; and a pressure sensitive adhesive layer disposed on a bottom surface of said member for providing releasable attachment of said dilator to said nose.

12. A nasal dilator for substantially preventing a nasal wall tissue of a nose of a wearer from drawing in during breathing, comprising: an elongated, flexible, substrate and a resilient member bonded thereto which provides a gentle expanding force to said nasal wall tissue when said dilator is adhesively attached to said nose; an adhesive layer disposed at least on a bottom surface of said substrate and an aromatic or transdermal substance disposed in a substantially segregated form bonded by an adhesive to an exterior surface of said dilator and being disposed within a body activated composition.

13. The nasal dilator of claim 12 wherein said aromatic or transdermal substance is disposed along with a hydrophilic or hydrophobic additive onto said elongated flexible substrate.

14. The nasal dilator of claim 12 wherein said body activated composition becomes substantially only activated upon being contacted by a human body.

15. A nasal dilator for substantially preventing a nasal wall tissue of a nose of a wearer from drawing in during breathing, comprising:

an elongated flexible, resilient member for providing a gentle expanding force to said nasal wall tissue when said dilator is adhesively attached to said nose;

a pressure sensitive adhesive layer disposed on a bottom surface of said dilator;

an aromatic substance disposed on a portion of said dilator;

said aromatic substance being disposed within a composition which is substantially only activated by the body of the wearer to deliver an inhaled amount of said aromatic substance through said nose which is perceived by the wearer to be sufficient to help the wearer breath easier or better.

16. A nasal dilator for substantially preventing a nasal wall tissue of a nose of a wearer from drawing in during breathing, comprising:

a thin, flexible, resilient member sized to fit across the nose of said wearer;

a pressure sensitive adhesive layer disposed on a bottom surface of said member for providing releasable attachment of said dilator to said nose; and an aromatic substance in a substantially segregated form affixed by an adhesive to an exterior surface of said resilient member, said aromatic substance disposed in an amount sufficient to be inhaled through said nose by the wearer.

17. The nasal dilator of claim 16 wherein said thin, flexible, resilient member comprises a breathable substrate and a spring member bonded thereto.

18. The nasal dilator of claim 16 wherein said aromatic substance is disposed in a quantity sufficient to provide a synergistic benefit to the wearer's breathing through a combination of mechanical dilation and inhalation of said aromatic substance.

19. The nasal dilator of claim 16 wherein said aromatic substance comprises: camphor, eucalyptus oil, peppermint oil, menthol, methylsalicylate, bornyl acetate, lavender oil, or a combination thereof.

20. A nasal dilator for substantially preventing a nasal wall tissue of a nose of a wearer from drawing in during breathing, comprising: a flexible, substrate, and a resilient member bonded thereto, said resilient member providing a gentle expanding force to said nasal wall tissue when said dilator is adhesively attached to said nose; a pressure sensitive, biocompatible adhesive layer disposed on a bottom surface of said substrate; and an aromatic medicated substance disposed in a substantially segregated form adhesively bonded to an exterior surface of said dilator, said aromatic medicated substance being provided in an amount sufficient to be inhaled through said nose of said wearer to help the wearer breath easier or better.

21. The nasal dilator of claim 20 wherein said aromatic medicated substance is disposed along with a hydrophilic or hydrophobic additive on said exterior surface of said dilator.

22. The nasal dilator of claim 20 wherein said adhesive bonding of said aromatic medicated substance comprises spraying said adhesive onto said flexible substrate.

* * * * *